United States Patent [19]
Allmann et al.

[11] Patent Number: 6,138,496
[45] Date of Patent: Oct. 31, 2000

[54] TRACTION MEASUREMENT APPARATUS AND METHOD

[75] Inventors: Erwin Ludwig Allmann, Penfield; Alan Robert Bentz, Bergen; Camiel John Raes, Phelps, all of N.Y.

[73] Assignee: Eastman Kodak Company, Rochester, N.Y.

[21] Appl. No.: 08/724,715

[22] Filed: Sep. 30, 1996

[51] Int. Cl.[7] .................................................. G01N 13/00
[52] U.S. Cl. ........................................................... 73/9
[58] Field of Search ............................. 73/8, 9, 104, 105, 73/146, 146.2, 146.3, 146.4, 146.5

[56] References Cited

U.S. PATENT DOCUMENTS

| | | | |
|---|---|---|---|
| 3,152,468 | 10/1964 | Powell | 73/8 |
| 3,520,180 | 7/1970 | Polhemus et al. | 73/146 |
| 3,813,917 | 6/1974 | Cole | 73/9 |
| 4,212,063 | 7/1980 | Hardmark | 73/9 |
| 4,324,128 | 4/1982 | Langer | 73/8 |
| 4,811,591 | 3/1989 | Antoine | 73/9 |
| 4,909,073 | 3/1990 | Takahashi et al. | 73/9 |
| 4,995,197 | 2/1991 | Shieh et al. | 73/8 |
| 5,113,688 | 5/1992 | Lazeration | 73/8 |
| 5,440,915 | 8/1995 | Storar | 73/9 |

FOREIGN PATENT DOCUMENTS

| | | |
|---|---|---|
| 535517 | 9/1992 | European Pat. Off. . |
| 5187993 | 7/1993 | Japan . |
| 1438182 | 6/1976 | United Kingdom . |
| WO 87/04235 | 1/1987 | WIPO . |

*Primary Examiner*—George Dombroske
*Attorney, Agent, or Firm*—Susan L. Parulski

[57] ABSTRACT

A measurement apparatus and method for determining the traction and coefficient of friction of a material on a roller. First and second rollers transport the material. Encoders are coupled to each roller, and a motor is coupled to one of the rollers. The motor applies a forward and reverse torque to the first roller, wherein the material slips relative to the roller. A computer coupled to the encoders calculates the traction and coefficient of friction.

13 Claims, 3 Drawing Sheets

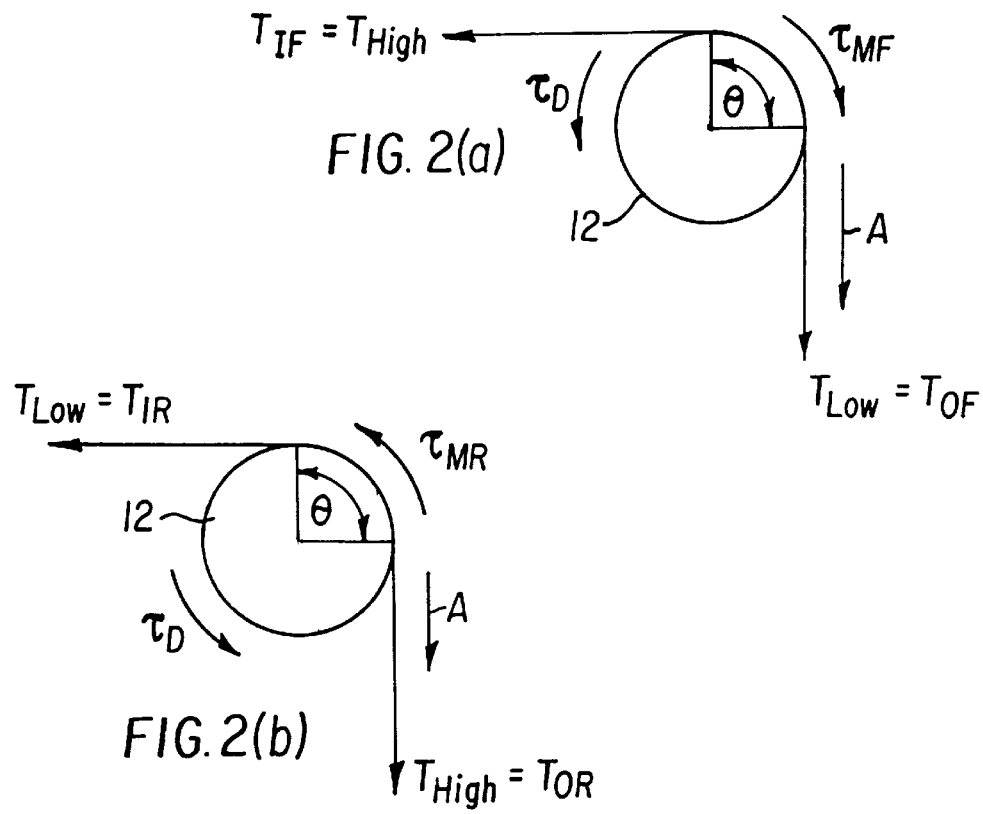
FIG. 2(a)
FIG. 2(b)
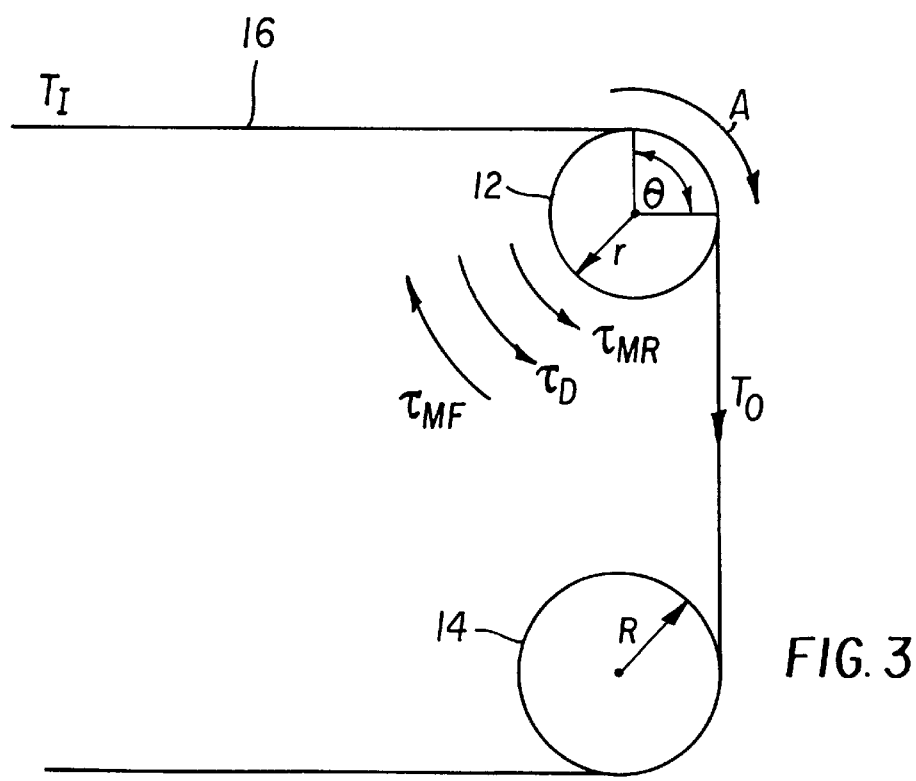
FIG. 3

TRACTION MEASUREMENT APPARATUS AND METHOD

FIELD OF THE INVENTION

The invention relates to a traction measurement apparatus and method, and to an apparatus and method for determining the coefficient of friction of a material on a roller.

BACKGROUND OF THE INVENTION

In the manufacturing of web material, the web material is typically transported by means of rotatable rollers. If the web material is sensitive to scratches and abrasions, such as photosensitive web material, care must be taken that scratches and abrasions do not occur as the web is transported. Such scratches and abrasions can occur if the web material "slips" on the roller. That is, if during transport of the web material by the rollers, the web material does not move at the same speed as the rotating roller, the web material may slip across the surface of the roller resulting in scratches and abrasions. As the speed of the web material is increased during transport, slippage is more likely to occur. Indeed, depending on a particular set of manufacturing parameters (including transport speed), it may not be possible to transport a specific web material at those parameters without slippage occurring.

Generally, traction refers to an adhesive or static friction. In a web handling environment, traction typically refers to the maximum web tension differential that can be supported across a roller without slippage occurring. Various factors can affect the traction, including tension levels of the web material, the angle of wrap of the web material on the roller, and the frictional properties of the web material and roller. By knowing the traction, slippage can be avoided.

U.S. Pat. No. 4,811,591 (Antoine) relates to a device for checking the surface condition of materials. Two identical wheels are positioned across the width of the material whose surface condition is to be checked. One of the wheels is braked until slip begins. The difference in the rotational speeds of the two wheels and the braking torque is determined. The braking torque provides an indication of the relative value of adhesion and surface condition.

U.S. Pat. No. 4,909,073 (Takahashi) relates to an apparatus for measuring the coefficient of friction between a wheel and a road surface, wherein the torque on a torsion bar interconnecting two wheels is monitored as one wheel's speed is changed until slippage occurs.

While these apparatus may have achieved certain degrees of success in a particular application, the apparatus are not suitable for an on-line, web transport manufacturing process. For example, the arrangement of the two wheels across the width of the material measures the coefficient of friction at a particular widthwise location, which may not represent the aggregate coefficient of friction of the web material. Further, such an arrangement of the two wheels tends to introduce lateral forces which may steer the material. Steering the material will adversely affect the movement of the web in a manufacturing process. In addition, forces which are significant at high speeds, such as viscous drag, air entrainment, and web material bending, need to be accounted for, as well as the ability to quickly recover from an induced slip condition.

Accordingly, a need continues to exist for an apparatus to determine the traction and coefficient of friction between a web and a surface. An automatic traction measurement apparatus and method which can be incorporated on-line in a web transport manufacturing process would ensure that adequate traction levels exist on the manufacturing process at all times, thereby avoiding problems relating to loss of traction. Such an apparatus and method should be capable of measuring the overall traction across the web, and should not adversely affect the manufacturing process or the web material. The apparatus should be suited for existing web transport rollers, account for forces which are significant at high speeds, and have the ability to quickly recover from a slip condition.

SUMMARY OF THE INVENTION

An object of the invention is to provide a traction measurement apparatus and method which can be used on-line during a manufacturing process.

Another object of the invention is to provide such an apparatus and method which can be used for handling web material, particularly web material which is photosensitive, and retrofitted to existing web transport rollers.

Still another object of the invention is to provide such an apparatus and method which can measure the coefficient of friction between the web material and a roller transporting the web material.

Yet another object of the invention is to provide such an apparatus and method which can compare the traction of various roller surfaces and web at various speeds of web material.

These objects are given only by way of illustrative example. Thus, other desirable objectives and advantages inherently achieved by the disclosed invention may occur or become apparent to those skilled in the art. The invention is defined by the appended claims.

According to one aspect of the invention, there is provided an apparatus for measuring a coefficient of friction of a material. The apparatus comprises a first roller adapted to contact the material to transport the material. Torque means, operatively coupled to the first roller, apply (i) a first torque in a first direction to the first roller to cause the material to slip relative to the first roller, and (ii) a second torque in a second direction opposite the first direction to the first roller to cause the material to slip relative to the first roller. Computer means control the motor and calculate the coefficient of friction. In an additional embodiment, the traction value is calculated. In a further embodiment, a second rotatable roller is employed which contacts the material to transport the material. Each of the first and second rollers has an axis of rotation, and the axes are substantially parallel and non-coaxial, with the second roller being unrestrained.

According to another aspect of the invention, there is provided a method for determining a traction value for a web of material being transported on a first rotatable roller. The method includes mounting a first roller for rotation about a first axis. The first roller contacts the web of material to transport the web of material. A speed ratio is continuously monitored. A first torque is applied in a first direction to the first roller. The value of the first torque which causes the web of material to slip relative to the first roller is then determined. Similarly, a second torque is applied to the first roller, however, the second torque is applied in a second direction opposite the first direction. The value of the second torque which causes the web of material to slip relative to the first roller is then determined. A coefficient of friction value and a traction value can be calculated using the first and second torque values. In another embodiment, a second rotatable roller is mounted for free rotation about a second axis of rotation; the second axis being substantially parallel to the first axis and the first and second axes being non-coaxial.

The present invention provides an automatic traction measurement apparatus and method which can be incorporated on-line in a manufacturing process, ensuring that adequate traction levels exist on the manufacturing process at all times so that problems relating to loss of traction can be avoided. The apparatus does not adversely affect the manufacturing process or the web material. Measurements made with the apparatus may be provided as an input to the manufacturing of the web material to improve its frictional characteristics. Further, the coefficient of friction can be a consideration in determining the operating speed of web handling equipment so as to prevent slippage.

BRIEF DESCRIPTION OF THE DRAWING

The foregoing and other objects, features, and advantages of the invention will be apparent from the following more particular description of the preferred embodiments of the invention, as illustrated in the accompanying drawings.

FIGS. 2(a) and 2(b) illustrate a tension differential in the web across a roller.

FIG. 3 shows a side view of a portion of the apparatus of FIG. 1.

DETAILED DESCRIPTION OF THE INVENTION

Figure 1:
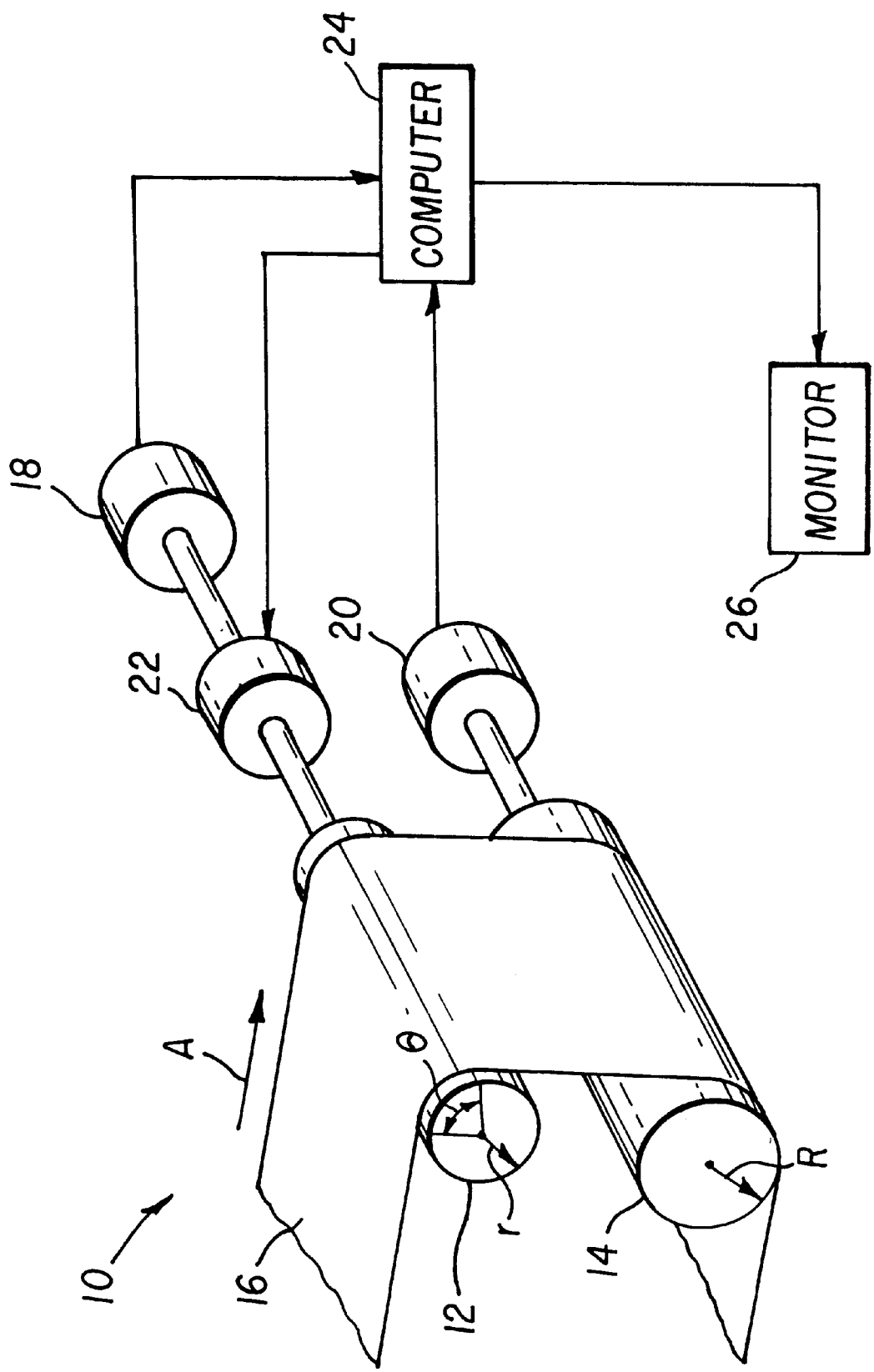
FIG. 1 shows a perspective view of a traction measurement apparatus in accordance with a first embodiment of the present invention.

The following is a detailed description of the preferred embodiments of the invention, reference being made to the drawings in which the same reference numerals identify the same elements of structure in each of the several figures.

FIG. 1 illustrates a first embodiment of a traction measurement apparatus 10. Apparatus includes a first roller 12 (i.e., a test roller) and a second roller 14 (i.e., a reference roller). Rollers 12,14 are each mounted for rotation about an axis. The axes of the rollers are substantially parallel, but are not co-axial. Second roller 14 is unrestrained, that is, freely rotatable about its axis. Preferably, rollers 12,14 are closely spaced. Web material 16 is transported across rollers 12,14 in a direction noted by arrow A, with a portion of web material wrapped about rollers 12,14. With such an arrangement of the rollers, measurement apparatus does not control the steering of the web material. Thus, apparatus can be used on-line since it does not adversely affect the manufacturing process.

The radius of first roller 12 is r, while the radius of second roller 14 is R. First and second rollers 12,14 need not be identical. The rollers may vary in their size, weight, and surface characteristics. Since the first and second rollers need not be identical, existing rollers in the manufacturing system can be utilized; no new rollers are required. In addition, the amount of wrap of the web about the roller may vary. The rollers typically have a length which is at least equal to or greater than the width of the web material. Using such full width rollers minimizes the occurrence of scratches on the web at the edges of the roller, whereas rollers with lengths narrower than the web width may cause scratches, abrasions, or marring.

Attached to each roller 12,14 is a means 18,20, respectively, of determining the speed of rotation of the respective roller. An example of such means 18,20 is an encoder. Other means 18,20 will be known to those skilled in the art for determining the speed of rotation of a roller. Hereinafter, speed determining means 18,20 will be referred to as encoders 18,20. First roller 12 further includes a torque source 22, such as a motor, for applying a torque to first roller 12. Hereinafter, torque source 22 will be referred to as motor 22. A computer means 24, for example a computer or microprocessor, controls the operation of traction measurement apparatus 10. A monitor 26 coupled with computer means 24 can provide a visual representation of the information being received or calculated by computer means 24.

At a constant web speed, and when no slip occurs, a torque acting on first roller 12 will result in a tension difference in the web across the roller, as illustrated in FIGS. 2(a) and 2(b) as $T_{high}$ and $T_{low}$ (units: pounds). The torque is canceled by the resulting tension differential across the roller. A ratio of the tension is $T_{high}/T_{low}$. For no slippage, the tension ratio can be up to a value of the $e^{f\theta}$, where $\theta$ is the angle of wrap of the web about the roller, and f is the coefficient of friction between the web and the roller. Thus, at the onset of slip:

$$T_{high}/T_{low}=e^{f\theta} \quad \text{(Equation 1)}$$

This equation relates the tensions on either side of the roller to the coefficient of friction and the wrap angle.

The value of the motor torque applied to first roller 12 at the onset of slippage is referred to as motor torque $\tau_M$ (units: inch-pounds). During operation, unknown drag torque $\tau_D$ (units: inch-pounds) may be present in the apparatus, such as from the drag from a roller bearing on which the roller is mounted, or from air entrainment in the apparatus.

The net torque $\tau_N$ is the sum of these two torque values. That is:

$$\tau_N=\tau_M+\tau_D \quad \text{(Equation 2)}$$

In the presence of unknown drag forces acting on first roller 12, to determine a coefficient of friction, two operations are performed to account for drag torque $\tau_D$: a forward operation and a reverse operation. Generally, in the forward operation, illustrated in FIG. 2(a), a measurement is made by progressively applying a forward motor torque $\tau_{MF}$ to first roller 12 until first roller 12 slips on web material 16. At the point of slip, the value of the forward motor torque $\tau_{MF}$ is noted; i.e., the value of the torque applied to first roller 12 when the slippage starts to occur. In the reverse operation, illustrated in FIG. 2(b), motor 22 acts as a brake, applying a progressively reverse motor torque $\tau_{MR}$ on first roller 12 until first roller 12 slips on web material 16; the reverse torque being in a direction opposite the forward torque. At the point of slip, the value of the reverse motor torque $\tau_{MR}$ is noted; i.e., the value of the torque applied to first roller 12 when the slippage starts to occur. The forward and reverse operations can be performed in any order. During the operation, computer means 24 controls the application of the torque and receives signals from encoders 18,20 relating to the speed of first and second rollers 12,14.

Encoders 18,20 are constantly monitored by computer means 24 while the forward and reverse torques are being applied to first roller 12. With the speed information from the encoders, computer means 24 can constantly determine a speed ratio S of first and second rollers 12,14. Speed ratio S can be calculated from the equation:

$$S=T_{14}/T_{12} \quad \text{(Equation 3)}$$

wherein $T_{14}$ is the period of encoder 20 associated with second roller 14; and $T_{12}$ is the period of encoder 18 associated with first roller 12. Slip is detected when a significant change in the speed ratio occurs. In the present invention, speed ratio changes in the range of 0.25% to 0.50% can be detected.

In operation, first and second rollers 12,14 are mounted and web material 16 is transported across the rollers. A known tension is applied to the web material. As speed ratio S is continuously monitored, forward motor torque $\tau_{MF}$ is progressively applied to first roller 12 until slip is detected. Motor 22 quickly recovers, and the value of forward motor torque $\tau_{MF}$ is stored by computer means 24. Similarly, reverse motor torque $\tau_{MR}$ is progressively applied to first roller 12 until slip is detected, wherein motor 22 quickly recovers and the value of reverse motor torque $\tau_{MR}$ is stored by computer means 24. The coefficient of friction f and traction is then calculated using the method described below.

Referring now to FIGS. 1, 2(a), and 3, in the forward operation, a known tension $T_{OF}$ is applied to the web material. Preferably, tension $T_{OF}$ is a substantially known constant tension applied to the web from externally applied tension control system (not shown) such as a load cell or float roll system controlling the transport of the web material. A tension $T_{IF}$ on web material 16 upstream from first roller 12 is reduced by drag torque $\tau_D$ and increased by forward motor torque $\tau_{MF}$ such that:

$$T_{IF}=T_{OF}-T_D+T_{MF} \qquad \text{(Equation 4)}$$

wherein:

$T_D$ is the tension drop across first roller 12 due to the drag torque such that $T_D=\tau_D/r$; $T_D$ is dependent on radius r of first roller 12 and is assumed to be a constant value for a given speed for the length of time over which the measurement takes place; and $T_{MF}$ is a tension difference resulting from the forward motor torque when slip occurs such that $T_{MF}=\tau_{MF}/r$.

Note that optionally, $T_{IF}$ can be a known constant tension value, and $T_{OF}$ can then be calculated. Similarly, either $T_{IF}$ or $T_{OF}$ can be measured.

Referring to FIG. 2(a), if $T\tau_{low}$ is substituted for $T_{OF}$, and $T_{high}$ is substituted for $T_{IF}$, then substituting Equation 4 into Equation 1 for no slippage during the forward operation, the relationship of the tension values to the coefficient of friction is:

$$\frac{T_{OF} - T_D + T_{MF}}{T_{OF}} = e^{f\theta} \qquad \text{(Equation 5)}$$

wherein the values of $T_D$ and the coefficient of friction f are unknown.

Referring now to FIGS. 1, 2(b), and 3, in the reverse operation, a known tension $T_{OR}$ is applied to the web material. Preferably, tension $T_{OR}$ is a substantially known constant tension applied to the web from externally applied tension control system (not shown) such as a load cell or float roll system controlling the transport of the web material. A tension $T_{IR}$ on web material 16 upstream from first roller 12 is reduced by drag torque $\tau_D$ and reverse motor torque $\tau_{MR}$ such that:

$$T_{IR}=T_{OR}-T_D-T_{MR} \qquad \text{(Equation 6)}$$

wherein $T_{MR}$ is a tension difference resulting from the reverse motor torque when slip occurs such that $T_{MR}=\tau_{MR}/r$.

Note that optionally, $T_{IR}$ can be a known constant tension value, and $T_{OR}$ can then be calculated. Similarly, either $T_{IR}$ or $T_{OR}$ can be measured.

If $T_{low}$ is substituted for $T_{IR}$, and $T_{high}$ is substituted for $T_{OR}$, then substituting Equation 6 into Equation 1 for no slippage during the forward operation, the relationship of the tension values to the coefficient of friction is:

$$\frac{T_{OR}}{T_{OR} - T_D - T_{MR}} = e^{f\theta} \qquad \text{(Equation 7)}$$

wherein the values of $T_D$ and the coefficient of friction f are unknown.

Equations 5 and 7 provide two equations with two unknowns, $T_D$ and the coefficient of friction f, allowing for the calculation of these values. Traction can then be determined; for the forward operation, traction is $T_{IF}-T_{OF}$, while for the reverse operation, traction is $T_{OR}-T_{IR}$.

If over time, the value of $T_D$ becomes sufficiently stable, then only one operation, either the forward or reverse operation, need be completed to calculate the coefficient of friction f.

Motor 22 can apply the torques in a variety of techniques: (i) as a progressively resisting force, (ii) as a constant resisting force, (iii) as a progressive co-operating force, and (iv) as a constant co-operative force.

Figure 4:
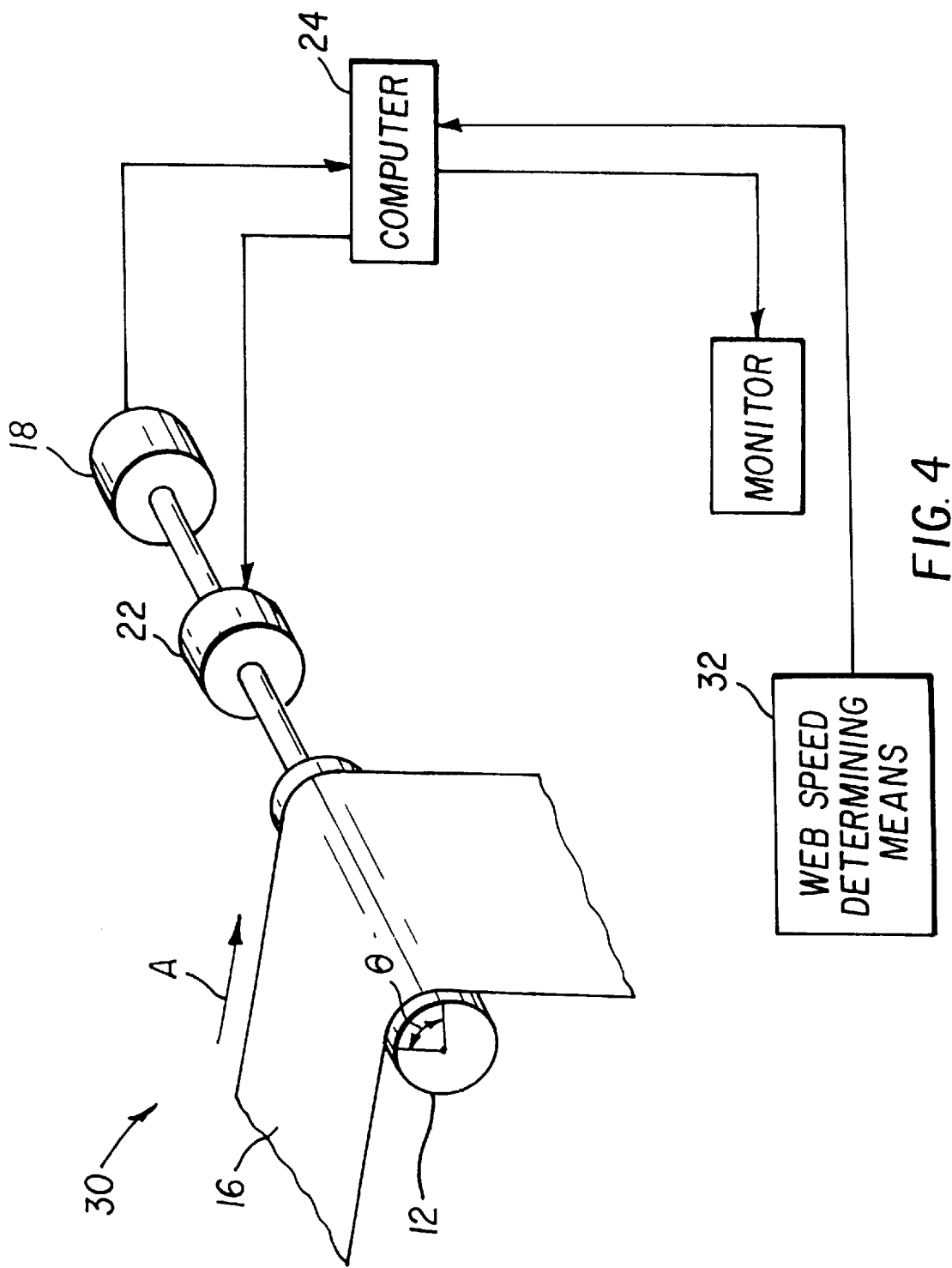
FIG. 4 shows a perspective view of a traction measurement apparatus in accordance with a second embodiment of the present invention.

In a second embodiment of a traction measurement apparatus 30 according to the present invention, illustrated in FIG. 4, a single roller, first roller 12, is employed. A web speed determining means 32, such as a non-contact device, for example a laser, determines the surface velocity of web material 16. The web speed can be determined at the location of first roller 12 or at any location within the transport system. A surface velocity of first roller 12 can be determined from speed determining means 18, which can be a non-contact device. Accordingly speed ratio S is calculated from the surface velocity of first roller 12 and the web speed of web material 16. That is:

S=surface velocity of first roller/speed of web material (Equation 8)

When the forward and reverse operations have been completed, Equations 5 and 7 provide two equations with two unknowns, $T_D$ and the coefficient of friction f, allowing for the calculation of these values. Traction can then be determined; for the forward operation, traction is $T_{IF}-T_{OF}$, while for the reverse operation, traction is $T_{OR}-T_{IR}$.

The present invention allows measurements of the coefficient of friction at different web speeds, and is suitable for high web speeds. High web speeds result in high drag torques, which, if not accounted for, result in inaccurate traction measurements. Drag torques have several sources: air entrainment in the nip, bearing drag, web bending, and air drag on the roller. Therefore, using the method of the present invention, normal roller drag is taken into account, and no special actions need be taken to account for it or to minimize it. Variations of $T_D$ over time are accounted for by the method of the present apparatus.

The invention has been described in detail with particular reference to a presently preferred embodiment, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

PARTS LIST 10 traction measurement apparatus
12 first roller; test roller
14 second roller; reference roller
16 web material
18 speed determining means; encoder
20 speed determining means; encoder
22 torque source; motor
24 computer means; microprocessor/computer
26 monitor
30 traction measurement apparatus
32 web speed determining means

What is claimed is:

1. An apparatus for measuring a coefficient of friction of a material, comprising:

a first rotatable roller adapted to contact the material to transport the material;

a second rotatable roller adapted to contact the material to transport the material, each of said first and second rollers having an axis of rotation, said axes being substantially parallel and non-coaxial, said second roller being unrestrained;

torque means operatively coupled to said first roller to apply (i) a first torque in a first direction to said first roller to cause the material to slip relative to said first roller, and (ii) a second torque in a second direction opposite said first direction to said first roller to cause the material to slip relative to said first roller;

means for detecting when slip occurs; and, computer means controlling said motor and calculating the coefficient of friction.

2. The apparatus according to claim 1 wherein said means for detecting when slip occurs comprises:

first speed determining means mounted to said first roller for determining a rotational speed of said first roller;

second speed determining means mounted to said second roller for determining a rotational speed of said second roller.

3. The apparatus according to claim 1 wherein the material has a first widthwise length and said first and second rollers have a second and third length, respectively, along their axes, and said second and third lengths are substantially equal to or greater than said first length.

4. The apparatus according to claim 1 wherein said first and second rollers vary in size, weight, or surface characteristics.

5. The apparatus according to claim 1 wherein said means for detecting when slip occurs includes:

first speed determining means for determining a surface velocity of said first roller; and second speed determining means for determining a speed of the material by non-contact with the material.

6. An apparatus for measuring a traction value for a web of transported material, comprising:

first and second independent rotatable rollers adapted to contact the web of material to transport the web of material, each of said rollers having an axis of rotation, said axes being substantially parallel and non-coaxial, said second roller being unrestrained;

torque means operatively coupled to said first roller to apply (i) a first torque in a first direction to said first roller to cause the material to slip relative to said first roller, and (ii) a second torque in a second direction opposite said first direction to said first roller to cause the material to slip relative to said first roller;

a first encoder mounted to said first roller for determining the speed of rotation of said first roller, and a second encoder mounted to said second roller for determining the speed of rotation of said second roller; and computer means controlling said motor, determining a speed ratio, and calculating the traction value.

7. The apparatus according to claim 6 wherein the material has a first widthwise length and said first and second rollers have a second and third length, respectively, along their axes, and said second and third lengths are substantially equal to or greater than said first length.

8. The apparatus according to claim 6 wherein said first and second rollers vary in size, weight, or surface characteristics.

9. A method for determining a coefficient of friction of a material, comprising:

mounting a first rotatable roller for rotation about a first axis, said first roller contacting the material to transport the material;

mounting a second rotatable roller for free rotation about a second axis of rotation, said second axis being substantially parallel to said first axis and said first and second axes being non-coaxial, said second roller contacting the material to transport the material, said second roller being unrestrained;

continuously monitoring a rotational speed of said first and second rollers;

progressively applying a first torque in a first direction to said first roller;

determining a value of said first torque which causes the material to slip relative to said first roller;

progressively applying a second torque in a second direction opposite said first direction to said first roller;

determining a value of said second torque which causes the material to slip relative to said first roller;

calculating the coefficient of friction from said first and second torque values.

10. The method according to claim 9 further comprising the step of calculating a traction value.

11. A method for determining a traction value for a web of material being transported on a first rotatable roller, comprising:

mounting said first roller for rotation about a first axis;

continuously monitoring a speed ratio;

applying a first torque in a first direction to said first roller;

determining a value of said first torque which causes the web of material to slip relative to said first roller;

applying a second torque in a second direction opposite said first direction to said first roller;

determining a value of said second torque which causes the web of material to slip relative to said first roller;

calculating a coefficient of friction value from said first and second torque values; and calculating the traction value.

12. The method according to claim 11 further comprising the steps of:

mounting a second rotatable roller for free rotation about a second axis of rotation, said second axis being substantially parallel to said first axis and said first and second axes being non-coaxial, said second roller being unrestrained, said first and second rollers contacting and transporting the web of material;

determining a rotational speed of said first roller;
determining a rotational speed of said second roller; and
calculating the speed ratio from the rotational speeds of said first and second rollers.

13. The method according to claim 11 further comprising the steps of:

determining a speed of the web material;
determining a surface velocity of said first roller;
calculating the speed ratio from said surface velocity and said web material speed.

* * * * *